United States Patent [19]

Suga et al.

[11] Patent Number: 4,758,381

[45] Date of Patent: Jul. 19, 1988

[54] 7,7,8,8-TETRACYANOQUINODIMETHANE AND METHOD FOR PREPARING THE SAME

[75] Inventors: Sadaharu Suga; Ayashi Noguchi; Shigeo Yasui, all of Okayama, Japan

[73] Assignee: Matsushita Electric Industrial Co., Ltd., Osaka, Japan

[21] Appl. No.: 833,862

[22] Filed: Feb. 24, 1986

[30] Foreign Application Priority Data

Feb. 23, 1985 [JP] Japan .................................. 60-35042

[51] Int. Cl.4 .............................................. C07C 50/06
[52] U.S. Cl. .................................. 260/396 N; 549/35
[58] Field of Search ....................... 260/396 N; 549/35

[56] References Cited

U.S. PATENT DOCUMENTS

| | | | |
|---|---|---|---|
| 3,115,506 | 12/1963 | Acker et al. | 260/396 N |
| 3,687,987 | 8/1972 | Martin | 260/396 N |
| 4,478,751 | 10/1984 | Jonas et al. | 260/396 N |
| 4,500,459 | 2/1985 | Hotta et al. | 260/396 N |
| 4,568,494 | 2/1986 | Jonas et al. | 260/396 N |

OTHER PUBLICATIONS

Wheland et al, *J. Org. Chem.*, vol. 40, No. 21, 1975, pp. 3101–3109, "Synthesis of Substituted 7,7,8,8-Tetraganoquinodimethanes".

*Primary Examiner*—Glennon H. Hollrah
*Assistant Examiner*—Raymond Covington
*Attorney, Agent, or Firm*—Wenderoth, Lind & Ponack

[57] ABSTRACT

A novel organic compound, 7,7,8,8-tetracyanoquinodimethane having a higher alkyl group containing at least ten carbon atoms, may be formed in a monomolecular layer or film by Langmuir-Blodgett's technique.

2 Claims, No Drawings

7,7,8,8-TETRACYANOQUINODIMETHANE AND METHOD FOR PREPARING THE SAME

BACKGROUND OF THE INVENTION

This invention relates to novel chemical compounds and to their preparation, and more particularly to 7,7,8,8-tetracyanoquinodimethane (hereafter referred to simply as TCNQ) compounds and method for the preparation of such compounds.

Recently integrated circuit technologies have remarkably progressed in the electronics field, and very large scale integrated circuits (VLSI) have been realized. However, the present technology for miniaturizing the integrated circuit is near the limit, and different approaches are required. For this purpose, various research of molecular electronics has been conducted.

Under the circumstances, the inventors thought that it was necessary to provide an organic compound which has electronic conductivity substantially equal to metals, and the molecules of which can be arranged in regular fashion. There are at present no organic compounds which have these characteristics.

Organic compounds, the conductivity of which are substantially equal to metals, are known such as a complex compound of TCNQ and tetrathiofulvalene (hereafter referred to as TTF). The complex compound is expressed by the following formula:

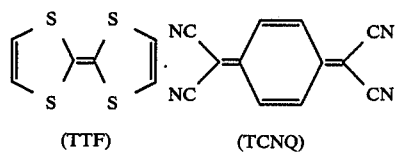

(TTF)          (TCNQ)

TCNQ and TTF form a charge-transfer complex because TCNQ is a strong electron acceptor and TTF is an electron donor. The complex has electric conductivity the maximum value of which is comparable with the electric conductivity of mercury. However, the complex of TTF and TCNQ has not been manufactured or processed in a monomolecular layer. Langmuir-Blodgett's technique is generally known in the art as a technique for arranging molecules in a monomolecular layer. However, generally known TCNQ derivatives cannot be processed in a monomolecular layer or film by the Langmuir-Blodgett technique.

Meanwhile, many studies have been directed to synthesize TCNQ derivatives. U.S. Pat. No. 3,558,671 discloses a method for synthesizing TCNQ fluoride and cyano TCNQ, in which quaternary ammonium salt is synthesized for use as dyestuff or pigment. U.S. Pat. No. 3,739,008 discloses a different method for synthesizing TCNQ fluoride and cyano TCNQ for use as dyestuff or antistatic agent. U.S. Pat. No. 3,687,987 discloses a method for synthesizing dialkoxyl TCNQ containing up to 8 carbons in the alkoxy groups. U.S. Pat. No. 3,526,497 discloses a method for synthesizing dialkoxyl TCNQ and dialkoxyl TCNQ fluoride, where the alkoxy groups contain up to 13 carbon atoms. U.S. Pat. No. 3,115,506 discloses a synthesizing method of TCNQ having an alkyl group of up to 8 carbons from alkyl substituted 1,4-cyclohexane-dione.

A method for synthesizing TCNQ having an alkyl group of up to 3 carbons is discussed in Journal of Organic Chemistry, vol. 28, p. 2719, 1963, in which 2-methyl-1,4-dimethoxybenzene obtained from 2-methyl-hydroquinone is reduced.

However, these synthesizing methods are unsuitable for a novel TCNQ product having higher alkyl group, because of small yield.

SUMMARY OF THE INVENTION

It is therefore an object of the present invention to provide novel organic compounds which have an electrical conductivity comparable with metals, and the molecules of which are capable of being arranged in regular fashion.

It is another object of the present invention to provide novel organic compounds which are able to form a monomolecular layer by Langmuir-Blodgett's technique.

It is a further object of the present invention to provide a method of synthesizing the novel organic compounds mentioned above.

The above objects can be achieved according to the invention by organic compounds which comprise TCNQ having a higher alkyl group.

These compounds are generally represented by the following formula:

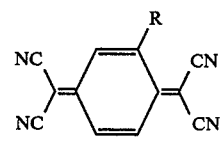

where R is an alkyl group containing 10 or more carbon atoms.

The compounds are synthesized by the steps of producing higher alkyl substituted cyclohexane-dione by hydrogenating higher alkyl substituted hydroquinone, reacting the higher alkyl substituted cyclohexane-dione with malononitrile, and oxidizing the resultant product.

DETAILED DESCRIPTION OF THE INVENTION

TCNQ is generally represented by the formula

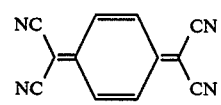

and is well known as an organic semiconductor having high electric conductivity. The organic compounds of the present invention are substitution products obtained by sustituting one of H atoms of TCNQ with a higher alkyl group which has 10 or more carbon atoms. The general formula of the organic compounds according to the present invention is represented by:

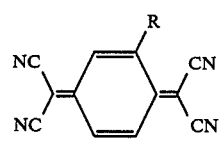

where R is a higher alkyl group containing not less than 10 carbons. When the alkyl group contains less than 10 carbons, it is difficult to make a membrane of the organic compounds by Langmuir-Blodgett's technique.

On the contrary, when the alkyl group contains 10 or more carbons, it becomes easy to make a membrane of the organic compounds by Langmuir-Blodgett's technique because of the substantial hydrophobic nature thereof. Higher alkyl groups of up to 22 carbons are practicable for the organic compounds.

When TCNQ having a higher alkyl group is dissolved in a solvent such as chloroform or benzene, the solution or mixture with higher fatty acid such as arachic acid may be formed as a monomolecular layer or film on the surface of water when dropped thereon. By the action of the higher alkyl group, TCNQ having the higher alkyl group is able to be formed as a monomolecular layer between the surface of the organic solution and the surface of the water, and therefore a monomolecular film or built-up film can be manufactured on a substrate by Langmuir-Blodgett's technique. The thus obtained monomolecular film or built-up film of TCNQ derivative forms a charge transfer complex compound with an electron donor such as TTF. The charge transfer complex compound is applicable for making various electronic devices.

TCNQ having a higher alkyl group is synthesized by the following steps.

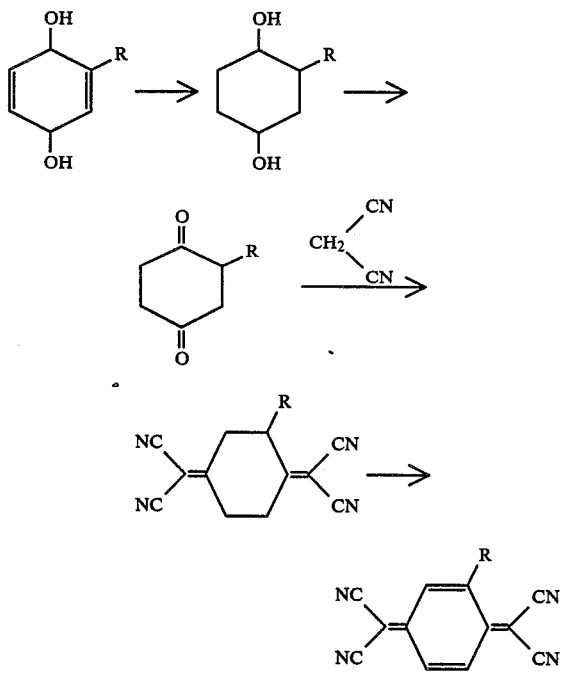

The synthesizing process starts from hydrogenation of hydroquinone having a higher alkyl group. The hydrogenation produces higher alkyl substituted 1,4-cyclohexane-diol which is then oxidized to the higher alkyl substituted 1,4-cyclohexanedione which is reacted with malonitrile and the product of the reaction is oxidized to produce TCNQ having a higher alkyl group.

The present invention will be practically explained by way of the following examples.

EXAMPLE 1 a. A process for preparing
2-dodecyl-1,4-cyclohexane-dione

A mixture of 20 g of 1,4-dimethoxy-2-dodecyl benzene, 30 ml of alcohol and 400 ml of diethyl ether was added into liquid ammonia at a temperature of −50° C. in a nitrogen stream.

Under stirring, 9.6 g of metallic sodium was added to react the mixture for 20 hours. After reaction, ammonia was removed, and an aqueous solution of ammonium chloride was added. This mixture was held at pH 2-3 by concentrated hydrochloric acid and was refluxed for 3 hours. After reflux, organic layer was separated from the water layer. The water layer was extracted by ethyl acetate and combined with the organic layer. The organic layer was rinsed with water, dried, and concentrated. After concentration, the organic layer was purified through silica gel column chromatography, and 2.0 g of 2-dodecyl-1,4-cyclohexane-dione was obtained. The obtained compound had a melting point of 73° C. and an infrared absorption band of 1710 cm$^{-1}$ which corresponds to a carbonyl group.

b. A process for preparing
1,4-bis-(dicyanomethylene)-2-dodecyl cyclohexane

A mixture of 2 g (0.0071M) of thus obtained 2-dodecyl-1,4-cyclohexane-dione and 1.4 g (0.0212M) of malononitrile was heated in a water bath to make a solution. β-alanine as a catalyst and 2 ml of water were added to the solution and stirred at a temperature between 40° C. and 50° C. for 8 hours to react the mixture. After cooling, the reacted mixture was dissolved in chloroform, and rinsed with water and dried. The dried material was concentrated under reduced pressure, and purified through silica gel column chromatography. As a result, 1.26 g of white crystal of 1,4-bis-(dicyanomethylene)-2-dodecyl cyclohexane was obtained. The obtained compound had a melting point of 97° C. and an infrared absorption band of 2250 cm$^{-1}$ which corresponds to a cyano group.

c. A process for preparing
2-dodecyl-7,7,8,8-tetracyanoquinodimethane 2.46 g (0.0065M) of thus obtained 1,4-bis-(dicyanomethylene)-2-dodecyl cyclohexane was dissolved in 90 ml of driedacetonitrile. In this solution, 30 ml of acetonitrile solution containing 3.55 g (0.0199M) of N-bromosuccinimide was dropped under ice cooling. After stirring at same temperature for 30 minutes, 1.6 ml (0.0198M) of pyridine was dropped into the mixture over the period of 10 minutes. The solution was stirred at room temperature for 10 minutes and poured into 100 ml of ice water. As a result, a crystal was separated. The separated crystal was filtered and purified through silica gel column chromatography. The purified crystal was recrystallized by ethyl acetate to obtain 1.28 g of 2-dodecyl-7,7,8,8-tetracyanoquinodimethane which was yellow acicular crystal.

The thus obtained TCNQ having a dodecyl group had the following characteristics.

Melting point: 120° C.
Infrared absorption band: 2250 cm$^{-1}$ (cyano).
Calculated for $C_{24}H_{28}N_4$: C 77.38%; H 7.58%; N 15.04%. Found: C 77.48%; H 7.87%; N 15.08%.

EXAMPLE 2

Twelve grams of 2-pentadecyl hydroquinone was dissolved in 100 ml of methanol. Then, the solution was hydrogenated in a hydrogen atmosphere having an initial pressure of 130 kg/cm$^2$ with Raney nickel as a catalyst at 170° C. reaction temperature. After cooling, the catalyst was removed and the solvent was volatilized to prepare a crystal of 2-pentadecyl-1,4-cyclohexane-diol. Then 8.7 g of the prepared crystal was dissolved in 200 ml of methylene chrolide with 26.6 g (0.001M) of complex of pyridinium chlorochromate and almina, and stirred for 2 hours under ice cooling. After filtration of oxidizing agent and volatilization of the solvent, 5.6 g of 2-pentadecyl-1,4-cyclohexane-dione, which was white scalelike crystal, was obtained by purifying through silica gel column chromatography.

The thus obtained compound had a melting point of 87° C. and an infrared absorption band of 1710 cm$^{-1}$ which corresponds to a carbonyl group.

The processes b and c of Example 1 were repeated using the obtained 2-pentadecyl-1,4-cyclohexane-dione as a starting material, whereby 1,4-bis-(dicyanomethylene)-2-pentadecyl cyclohexane which had a melting point of 98° C. and 2-pentadecyl-7,7,8,8-tetracyanoquinodimethane were obtained. The yield of the 1,4-bis-(dicyanomethylene)-2-pentadecyl cyclohexane and 2-pentadecyl-7,7,8,8-tetracyanoquinodimethane were 72% and 46.2% respectively. The thus obtained TCNQ having a pentadecyl group had a melting point of 120.5° C. and an infrared absorption band of 2250 cm$^{-1}$ which corresponds to a cyano group.

EXAMPLE 3

The processes of Example 2 were repeated except that 2-octadecyl hydroquinone was used instead of 2-pentadecyl hydroquinone. The resultant materials of each reaction were as follows:

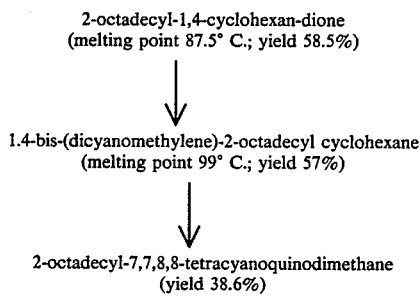

2-octadecyl-1,4-cyclohexan-dione
(melting point 87.5° C.; yield 58.5%)

↓

1.4-bis-(dicyanomethylene)-2-octadecyl cyclohexane
(melting point 99° C.; yield 57%)

↓

2-octadecyl-7,7,8,8-tetracyanoquinodimethane
(yield 38.6%)

The thus obtained TCNQ having a octadecyl group had a melting point of 125.5° C. and an infrared absorption band of 2250 cm$^{-1}$ which corresponds to a cyano group.

TCNQ having a higher alkyl group synthesized by methods such as those described above is able to be formed in a monomolecular layer or film by Langmuir-Blodgett's technique. Now, an example of this will be explained. TCNQ having a dodecyl group obtained by Example 1 was dissolved in chloroform to make a solution of molarity of 10$^{-4}$M. In this case, TCNQ was used singly or in dilute solution with higher fatty acid such as arachic acid. When the solution was dropped on a surface of an aqueous solution of pH 5.5 in which $4\times10^{-4}$ mol of cadmium chloride and $5\times10^{-4}$ mol of potassium hydrogencarbonate were dissolved, TCNQ having the dodecyl group was spread on the surface of the aqueous solution to make a good monomolecular layer or film. The monomolecular layer or film may form a built-up film by piling on one after another of the monomolecular layers.

As described above, TCNQ having a higher alkyl group may be formed into a Langmuir-Blodgett's membrane. Therefore, it is possible to make a complex compound of TCNQ having a higher alkyl group and an electron donor such as TTF, heterocyclic quaternary ammonium salt, cyanine-dye, etc. as a very thin film having conductivity comparable with metals.

The very thin film is useful for various devices in the molecular electronics field, such as organic semiconductor devices, light memory devices, photo-electric devices and so on. For example, N-butylpyridinium (TCNQ)n complex shows resistivity-temperature characteristics in which the resistivity abruptly varies near 100° C. Therefore, the complex may be applicable to a temperature detector which is to be integrated in very large scale.

What is claimed is:

1. A 7,7,8,8-tetracyanoquinodimethane compound represented by the following formula

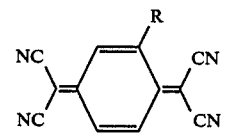

in which R represents alkyl of 10–22 carbon atoms.

2. An organic charge transfer complex comprising:
an electron acceptor of a 7,7,8,8-tetracyanoquinodimethane compound represented by the following formula

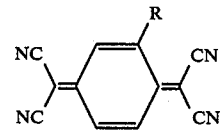

in which R represents alkyl of 10–22 carbon atoms, and
an electron donor selected from the group consisting of tetrathiofulvalene, heterocyclic quaternary ammonium salt, and cyanine-dye.

* * * * *